US012636013B2

(12) United States Patent
Aubert et al.

(10) Patent No.: US 12,636,013 B2
(45) Date of Patent: May 26, 2026

(54) MEDICAL-GRADE ACTUATOR HAVING A MODULAR STRUCTURE AND MEDICAL DEVICE COMPRISING SAME

(71) Applicant: MYOPOWERS MEDICAL TECHNOLOGIES FRANCE SAS, Besancon (FR)

(72) Inventors: Christophe Aubert, Cudrefin (FR); Fabian Kaegi, Lausanne (FR); Francois Cabaud, Ecole Valentin (FR)

(73) Assignee: MYOPOWERS MEDICAL TECHNOLOGIES FRANCE SAS, Besancon (FR)

( * ) Notice: Subject to any disclaimer, the term of this patent is extended or adjusted under 35 U.S.C. 154(b) by 1256 days.

(21) Appl. No.: 16/768,657

(22) PCT Filed: Nov. 30, 2017

(86) PCT No.: PCT/IB2017/001699
§ 371 (c)(1),
(2) Date: May 30, 2020

(87) PCT Pub. No.: WO2019/106403
PCT Pub. Date: Jun. 6, 2019

(65) Prior Publication Data
US 2021/0169490 A1 Jun. 10, 2021

(51) Int. Cl.
*A61B 17/12* (2006.01)
*A61B 17/00* (2006.01)
*A61F 2/00* (2006.01)
(52) U.S. Cl.
CPC .................. *A61B 17/12013* (2013.01); *A61B 2017/00477* (2013.01); *A61F 2/0036* (2013.01)

(58) Field of Classification Search
CPC .............. A61B 17/12; A61B 17/12009; A61B 17/1322; A61B 2017/320056;
(Continued)

(56) References Cited

U.S. PATENT DOCUMENTS 5,554,139 A * 9/1996 Okajima ............. A61M 25/005
600/433
8,876,694 B2 * 11/2014 Honaryar .............. A61F 5/0056
600/37
(Continued)

*Primary Examiner* — Kathleen S Holwerda
*Assistant Examiner* — Lauren Dubose
(74) *Attorney, Agent, or Firm* — GRGO Global; Steven M. Greenberg

(57) ABSTRACT

The present invention relates to an artificial contractile device comprising at least one contractile element (1) comprising a flexible strip (4) extending in a longitudinal direction and a closure (6) for forming the contractile element (1) into a closed loop around a hollow body organ, the closure (6) being situated at a first extremity of the flexible strip (4). The contractile element is adapted to contract a hollow body organ, in such a way that said contractile element (1) may be in a resting position or in an activated position. The artificial contractile device further comprises a flexible transmission (3) comprising a tensioning element (31) being anchored at a first end (311) to a first anchoring point (A) on the flexible strip (4), said flexible transmission (3) being adapted to tighten the contractile element (1) formed in a closed loop around said hollow body organ upon application of a traction force at and end of the tensioning element (2031) by an actuator (7). The artificial contractile device also comprises a connector (5) adapted to connect the flexible transmission (Continued)

(3) to a said actuator (7), a second end (312) of said tensioning element (2031) being anchored in said connector (5).

18 Claims, 4 Drawing Sheets

(58) Field of Classification Search
CPC ..... A61B 17/295; A61B 17/285; A61B 17/08; A61B 17/12013; A61B 17/12022; A61B 17/1327; A61B 2017/00411; A61B 2017/00477; A61B 2017/00827; A61B 2017/00876; A61F 6/20; A61F 5/005; A61F 2/0036; A61F 2/0054; A61F 2250/0001; A61F 2250/001; A61F 5/0059; A61F 6/202; A61F 2/004; A61F 2/08; A61F 2/48; A61F 2002/044; A61F 2002/0894; A61F 2005/0016; A61F 2005/414; A61F 2210/0033; A61F 2210/009; A61F 2220/0008; A61F 2230/0013; A61F 2250/0002; A61F 2250/0003; A61F 2250/0004; A61F 2250/0013; A61F 5/0003; A61F 5/003; A61F 5/0033; A61F 5/0053; A61F 5/0056; A61F 5/0063; A61F 5/0066; A61F 5/0079; A61F 5/0089; A61F 5/48; A61M 60/122; A61M 60/268; A61M 60/40; A61M 2205/0283; A61M 60/50; A61M 2205/33; A61M 2205/3303; A61M 2205/8243; A61M 60/148; A61M 60/857; A61M 60/871
USPC ......................................................... 606/157
See application file for complete search history.

(56)                    References Cited

U.S. PATENT DOCUMENTS

| | | | |
|---|---|---|---|
| 2010/0305397 A1* | 12/2010 | Birk ...................... | A61F 5/0063 |
| | | | 600/37 |
| 2012/0022320 A1* | 1/2012 | Hendrickx .............. | A61F 5/005 |
| | | | 600/37 |
| 2012/0123196 A1 | 5/2012 | Rion et al. | |
| 2012/0184980 A1* | 7/2012 | Anderson ............. | A61F 2/0036 |
| | | | 606/192 |
| 2013/0096586 A1 | 4/2013 | Tozzi et al. | |
| 2013/0296900 A1* | 11/2013 | Szewczyk ........ | A61B 17/12022 |
| | | | 606/157 |
| 2014/0371855 A1* | 12/2014 | Clement .............. | A61F 2/0036 |
| | | | 623/14.13 |
| 2016/0374687 A1 | 12/2016 | Wieland et al. | |

* cited by examiner

MEDICAL-GRADE ACTUATOR HAVING A MODULAR STRUCTURE AND MEDICAL DEVICE COMPRISING SAME

CROSS-REFERENCE TO RELATED APPLICATIONS

This application is a § 371 national phase entry of International Application No. PCT/IB2017/001699, filed Nov. 30, 2017, the entirety of which is incorporated herein by reference.

TECHNICAL FIELD

The present invention relates to the field of implantable medical devices, in particular medical devices comprising an artificial contractile structure for occluding a hollow body organ.

STATE OF THE ART

In order to treat conditions such as urinary incontinence, faecal incontinence, gastro-oesophageal reflux disease and also for the treatment of obesity by gastric banding, medical devices are often implanted into the patient which comprise an artificial contractile structure, often known as a cuff, attached around a hollow body organ such as the urethra, rectum, oesophagus or the stomach. In order to reduce the diameter of the organ in question or to occlude it, the artificial contractile structure applies pressure thereto. Particularly in the case of urinary or faecal incontinence, the contractile structure essentially creates an artificial sphincter which can be opened and closed by controlling the pressure applied by the cuff.

In such applications, it is extremely important to apply this pressure as gently as possible so as to avoid damaging the organ. Currently, this is usually carried out by inflating a tube or balloon-type structure arranged on the inside of the contractile element and which applies pressure on the organ. A commercially successful example of this type of device is the AUS 800 marketed by American Medical Systems, Inc. This device and its predecessors are described in U.S. Pat. Nos. 3,863,622, 4,222,377, 4,412,530, and 4,878,889. When applied for the treatment of urinary incontinence, this device has a silicone pressure regulating balloon implanted in the perivesical space, a silicone control pump implanted in the scrotum or labia and a silicone urethral occlusive cuff wrapped around the bulbous urethra in males or the bladder neck in females. Each component may be filled with saline or radiopaque contrast media, and tubing emanating from each component may be routed between incisions for appropriate connections. The patient operates the device by squeezing the control pump through the scrotal or labial skin, and this action transfers fluid from the cuff to the pressure regulating balloon in order to release pressure on the urethra and permit urination, after which the balloon forces fluid through a restrictor and back into the contractile element so as to re-establish an occlusive urethral pressure within 3 to 5 minutes. Furthermore, the device can be deactivated to allow tissue healing to proceed and urethral edema to subside or before inserting a catheter or other instrument into the urethra.

However, this type of device is extremely complicated to implant since three inter-operating components need to be assembled and filled with fluid in situ, and upon inflation it can fold or change its shape in a non-uniform manner, thereby creating so-called "pillows" which can cause a non-uniform pressure to be applied. Furthermore, they are prone to fluid leakage and may cause urethral atrophy and erosion. Fluid leaks may also cause complications such as post-operative infection requiring maintenance or replacement of the device.

Various attempts have been made in the past at designing non-hydraulic cuffs which do not suffer from the above limitations. For instance, U.S. Pat. No. 6,074,341 describes a medical device comprising a non-hydraulic cuff which is spring-biased in the occluded position. Tension applied to a wire member by the actuator counteracts the spring bias so as to open the cuff. Upon releasing the tension, the spring bias returns the cuff to its occluded position. This arrangement raises safety concerns, since in the case of a malfunction of the actuator the patient would not be able to urinate and would hence require immediate emergency surgery to prevent kidney damage. US 2012/0184980 describes a medical device comprising a different non-hydraulic cuff structure, in which the cuff is formed as a sheath arranged around the urethra, and wherein a tape arranged inside the sheath is attached to an actuator and is pulled so as to tighten the cuff and apply occlusive pressure to the urethra. However this cuff is complicated and bulky. Yet further examples include US 2012/0296157, which describes medical devices comprising extremely simple wire-actuated cuffs, WO13093074, which describes soft rubber cuffs actuated by wires, and EP 1 547 549 which describes cuffs tightened by twisting a pair of wires situated inside the cuff. A gentle, uniform application of pressure to an organ does not appear to be achievable with any of these three latter examples.

An object of the invention is thus to overcome at least partially some of the above-mentioned drawbacks of the prior art.

DISCLOSURE OF THE INVENTION

The object of the invention is attained by an artificial contractile structure comprising at least one contractile element comprising a flexible strip extending in a longitudinal direction and a closure for forming the contractile element into a closed loop around a hollow body organ, the closure being situated at a first extremity of the flexible strip, the contractile element being adapted to contract a hollow body organ, in such a way that said contractile element is adapted to be in a resting position or in an activated position, the activated position being defined with said contractile element constricting the hollow body organ and the resting position being defined with said contractile element not constricting the hollow body organ.

According to the present invention, said artificial contractile device further comprises:

a flexible transmission comprising a tensioning element being anchored at a first end to a first anchoring point on the flexible strip, said flexible transmission being adapted to tighten the contractile element formed in a closed loop around said hollow body organ upon application of a traction force at and end of the tensioning element by an actuator, and a connector adapted to connect the flexible transmission to a said actuator, a second end of said tensioning element being anchored in said connector.

In consequence, the medical device applies a gentle, uniform pressure to the hollow body organ, without localised pressure spikes, thereby reducing its impact on the underlying tissue, reducing damage thereto.

In addition, the device of the invention is extremely easy to implant in a patient and to safely or disconnect from an actuator thanks to the provision of the connector, advantageously of a push-fit, plug & play type.

In an embodiment, the tensioning element is covered with a flexible sheath.

In an embodiment, the flexible strip comprises a plurality of transversal reinforcement elements extending from a surface thereof opposite a smooth surface arranged for contacting said hollow body organ.

In an embodiment, the flexible strip comprises a plurality of openings, each opening being situated between two adjacent transversal reinforcement elements.

In an embodiment, the tensioning element is a filament, a wire, a cable or a flat strip.

In an embodiment, the tensioning element passes through at least some of the transversal reinforcement elements.

In an embodiment, the sheath comprises at least one coiled wire.

In an embodiment, the sheath comprises an inner coiled wire coiled in a first direction, and an outer coiled wire surrounding the inner coiled wire and coiled in a second direction opposite to said first direction.

In an embodiment, the closure is arranged so as to form the contractile element into a closed loop having one of a plurality of predetermined circumferences.

In an embodiment, the closure comprises a tab at an end of the flexible strip and connected thereto by two connecting side walls integrally formed with the tab and flexible strip in order to define a pass-through hole for passing said flexible transmission and connector to form the contractile element in a closed loop around said hollow body organ.

In an embodiment, the connector is configured for allowing push-fit connection to an actuator.

In an embodiment, said push-fit connector comprises a helicoidal spring or an o-ring linking a first annular groove provided in one of said actuator and said connector and providing a kinematic link with a further annular groove provided in another of said actuator and said connector.

In an embodiment, the connector comprises a connecting rod longitudinally movable within a coaxial plug, said connecting rod being attached to said tensioning element (31).

In an embodiment, connecting rod comprises a crenelated part cooperating with releasable hooking members of said plug to allow movement of the connecting rod in said plug.

The object of the invention is also attained by a medical device comprising an artificial contractile structure as described above and an actuator comprising a connection socket configured for push-fit connection with said connector, said actuator comprising an actuating mechanism arranged to apply a tensile force to said tensioning element of the flexible transmission when said connector is connected into said socket.

BRIEF DESCRIPTION OF THE DRAWINGS

The invention will now be further described with reference to the figures, which show.

4

Figure 4:
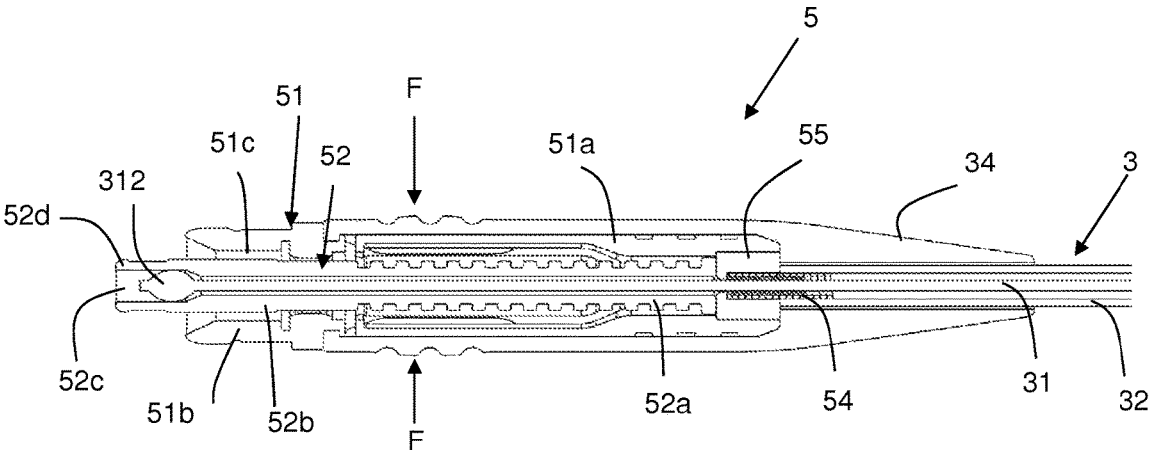
Figure 5:
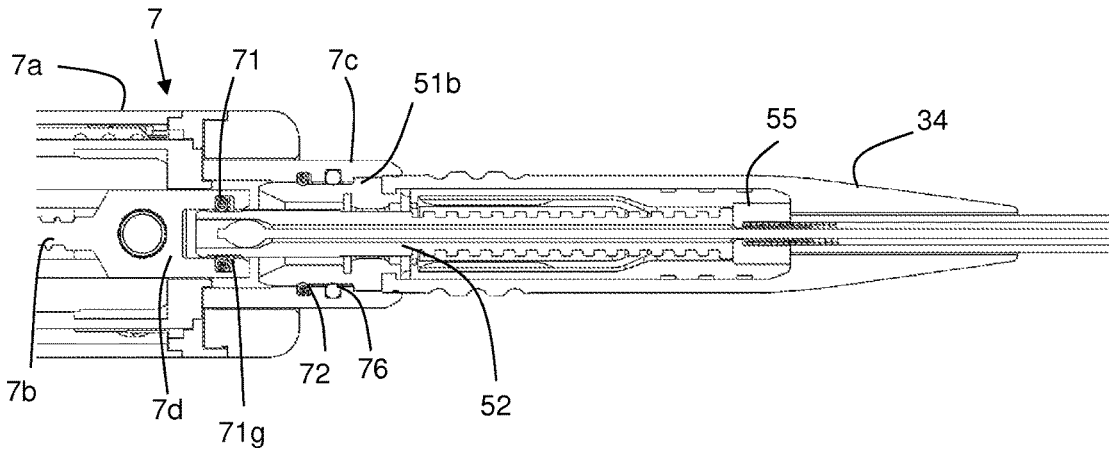
Figure 6:
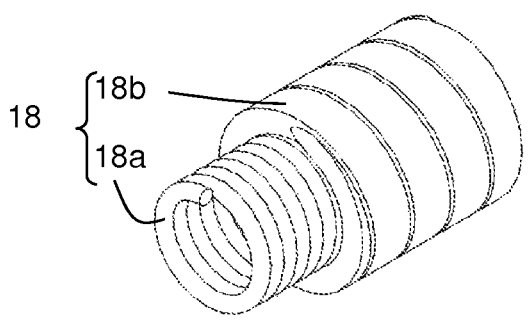

FIG. 4: a longitudinal cross-sectional view of the connector of the artificial contractile device of the invention;

FIG. 5: a longitudinal cross-sectional view of the connector of the artificial contractile device of the invention connected to a screw type actuator;

FIG. 6: a perspective view of a section of a wire coil element of a sheath for the tensioning device of the artificial contractile device of the invention.

EMBODIMENT OF THE INVENTION

Figure 1A:
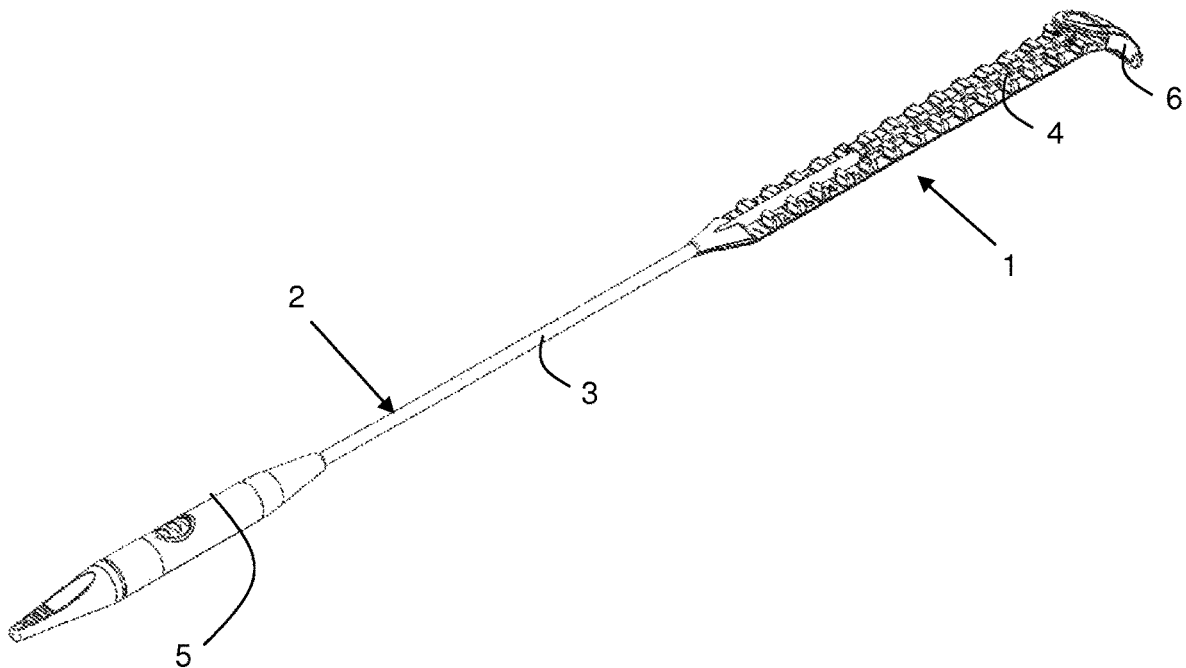
FIGS. 1A and 1B: a perspective view of an artificial contractile device according to the invention with an open contractile element assembled with its tensioning device and connector.
Figure 1B:
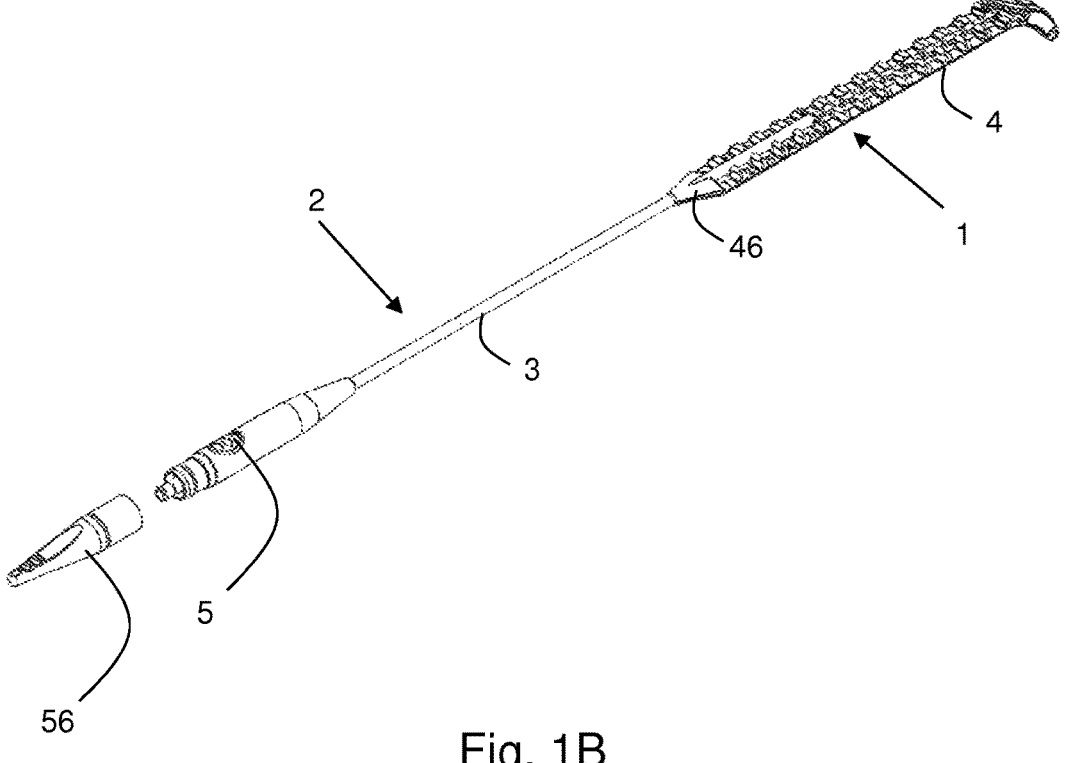

FIGS. 1A and 1B illustrates part of an artificial contractile device according to the invention, in particular a contractile element 1, otherwise known as a cuff, assembled together with a tensioning device 2. In the view of FIG. 1, contractile element 1 is illustrated in its open position, i.e. its position before being applied around a hollow body organ. Contractile element 1 comprises a flexible strip or ribbon 4 extending in a longitudinal direction, and constructed e.g. from implant grade silicone elastomer of sufficient Shore hardness, e.g. of between 40 and 80 Shore A, preferably between 50 and 43 Shore A. As non-limiting examples, liquid silicone elastomers from the company Nusil can be used, for instance MED-4843 with shore A hardness 43, MED-4860 with shore A hardness 60, or MED-4850 with shore A hardness 50. Alternatively, polyurethane or other flexible, biocompatible thermoplastic materials may be used instead of, or additionally to, silicone elastomer.

A plurality of transversal reinforcement elements 42 are arranged along flexible strip 4, evenly spaced and numbering in the present example, however the number and the spacing can be chosen according to the needs of the skilled person. Transversal reinforcement elements 42 are aligned substantially perpendicular to the above-mentioned longitudinal direction and show a substantially curved shape, although other forms are also possible. Advantageously, openings 43 are provided between pairs of adjacent transversal reinforcement elements 42. In the present example, these openings 43 are formed as slots between some of the transversal reinforcing elements 42. These openings 43 of generally rectangular form are disposed on the centreline of the contractile element 1 and extend towards its edges. Other forms of openings 43 are of course possible. The openings 43 serve to reduce the tensile force required to apply force to the hollow body organ, since less contractile element material needs to be compressed when the contractile element 1 is actuated.

Figures 2, 3:
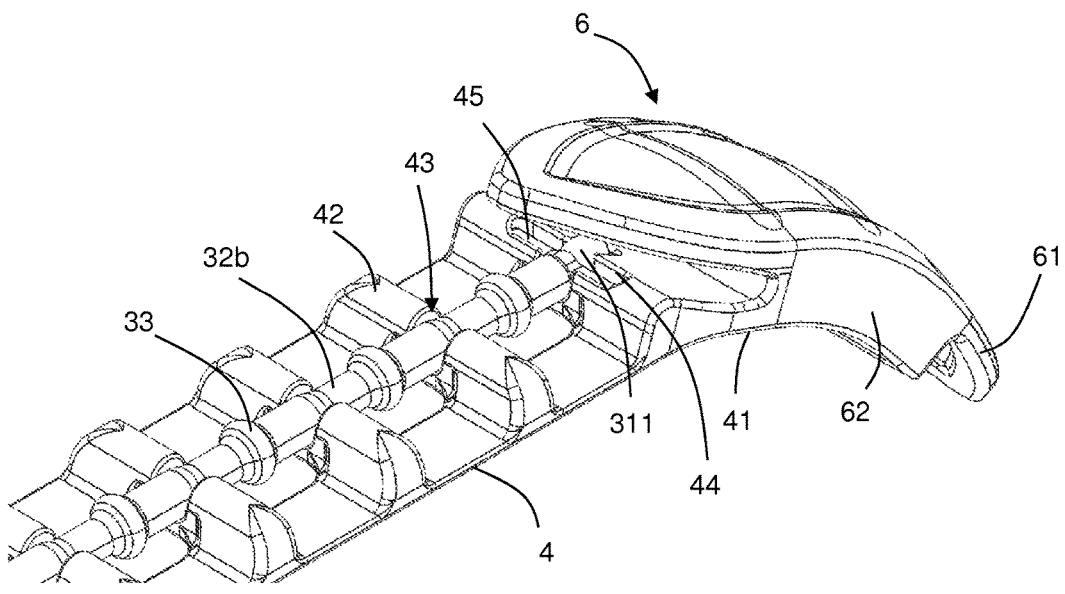
FIG. 2: a perspective, close-up view of a closure end of the contractile element of the artificial contractile device of the invention.
FIG. 3: a longitudinal cross-sectional view of the contractile element of the artificial contractile device of the invention.

At the distal end of flexible strip 4 is provided a closure 6, shown in more details in FIGS. 2 and 3. Said closure 6 comprises a tab 61 extending at a free end of the flexible strip 4 and connected thereto by means of two connecting side walls 62 integrally formed with the tab 61 and an end flap 41 of the strip 4. The tab 61, walls 62 and flap 41 define a pass-through hole 63. The closure 6 is thus arranged so as to be able to form the contractile element 1 into a closed, substantially circular cuff around a hollow body organ by rolling the flexible strip 4 about a said hollow body organ and passing the opposite free end of the artificial contractile device comprising a connector 5 through the pass-through hole 63 in order to tighten the contractile element 1 to a desired diameter around it.

Advantageously, the tab 61 comprises an inner surface facing the flap 41 slots 64 adapted for cooperating in a snap-fit fashion with the reinforcement elements 42 on the flexible strip 4 to lock the strip in place at a desired constricting diameter when rolled about the hollow body organ.

When in place about a hollow body organ in its closed position the maximum circumference of contractile element 1 may be for instance 6 cm for implanting around a male urethra, or 11 cm for implanting around the bladder neck in females. However, other minimum and maximum circumferences are of course possible. As an example, the width of the flexible strip 4 may be between 7 and 10 mm, however naturally larger and smaller widths are likewise possible. As previously described, the closure 6 is arranged so as to be closed at a number of discrete closing positions, or alternatively may be arranged so that it can be closed at any convenient point along the flexible strip 4.

The artificial contractile device of the invention further comprises a tensioning device 2 comprising a flexible transmission 3 extending between said contractile element 1 and said connector 5 to apply a tensile force to the contractile element 1 through an actuator to which connector 5 is attached.

Flexible transmission 3 comprises a core of a wire 31 surrounded by a sheath. The sheath comprises an outer sheath 32, e.g. of silicone elastomer, covering a wire coil 18 (FIG. 6), which covers the wire 31, broadly following the construction of a Bowden cable. In consequence, pulling or pushing on wire 31 will cause it to move with respect to the sheath. The wire 31 may be e.g. of stainless steel or other metal alloys (e.g. SS 304V, 316L, MP35N, MP35NLT), and may be housed in or coated with an ePTFE or PTFE tube or coating to reduce friction. Additionally, the number and diameter of the strands composing the wire 31 should be chosen to minimise friction, and the wire may also be redrawn so as to make its surface smooth and coated with PTFE or similar lubricant materials. Alternatively, the wire 31 may be made of titanium, Nitinol, or any other convenient biocompatible metal, or a polymer such as PTFE, Aramid, ultrahigh molecular weight polyethylene (e.g. as sold by Dyneema), or similar. Wire 31 may also be flat or oval in cross-section, and may even be of variable cross-section, e.g. circular within the wire coil 18, and flat within the contractile element 1. Alternatively, a cable, of either circular or flat cross-section, could be used instead of the wire.

Outer sheath 32 comprises a thicker proximal part 32a (with respect to connector 5) covering flexible transmission 3 from the connector 5 to a more rigid, proximal end of flexible strip 4 connecting it to flexible transmission 3 and a thinner, flexier, distal part 32b (with respect to connector 5) extending until closure 6 as described herein after. Both proximal and distal parts 32a, 32b are attached to the contractile element 1 by push-fitting it into the openings 43 between reinforcement elements 42. The wire 31 projects from the outer sheath 32 and wire coil 18 at a distal first end where an anchoring knot 311 is formed, which knot 311 is securely fitted into an anchoring slot 44 of the flexible strip 4, located close to the closure 6. The knot 311 may be glued into the corresponding anchoring slot 44 or preferably associated with a first retaining plate 45, forming a first anchoring point A. Sheath 16 is further secured at a second anchoring point B, located at the interface between proximal and distal parts 32a, 32b of sheath 32. Said second anchoring point B may be formed by a second retaining plate received in a second anchoring slot arranged in reinforcement elements 42. Second retaining plate and second anchoring slot are not shown in the figures. First and second retaining plates may be of metallic biocompatible material soldered to the wire coil 18, and the wire 20 remains free to slide through the coil 18 as described hereinafter.

Still preferably, the outer sheath 32 is fully secured to the flexible strip 4 by gluing it or overmoulding it in the constituting material of the strip 4 after positioning of the sheath 32 as explained above, said gluing, overmoulding further allowing formation of a reinforcing end cap 46 for the strip 4 from which the proximal part 32a of sheath 32 further extends over the wire coil 18 until connector 5 as described hereinafter.

The opposite end of tensioning device 2, which comprises connector 5, represented in FIG. 4, is arranged to be attached through that connector 5 to an appropriate actuator 7, partly visible in FIG. 5, such as that described in WO13091730, WO13093074 or WO12000681, herein incorporated by reference in their entirety. A force applied by the actuator 7 to wire 31 through connector 5 causes it to slide within wire coil 18 of the flexible transmission 3, inducing a longitudinal contraction of the flexible strip 4 of the contractile element 1, which provides the contractile effect on a hollow body organ when said contractile element 1 is looped around such.

FIGS. 4 and 5 illustrate a push-fit connector 5 for attaching the flexible transmission 3 comprising wire 313 of tensioning device 2 to an actuator 7.

The illustrated actuator 7 comprises a housing 7a inside which a screw-type mechanism 7b is mounted. Naturally, other types of mechanism 7b are possible.

In order to simplify assembly of the entire system in situ, i.e. inside a body cavity of the patient, the attachment of the connector 5 to the actuator 7 is carried out by means of push-fit joints, as will be explained in more detail below.

As illustrated in FIGS. 4 and 5, a second end of wire 31, i.e. the end opposite to that forming knot 311 hold in anchoring slot 44 of strip 4, also comprises an anchoring knot 312 which is secured to a plug 51. Plug 51 comprises a substantially cylindrical body 51a, extending longitudinally within a cavity of a protective shell 34 made of same biocompatible flexible material as sheath 32 and flexible strip 4 preferably, in particular a silicon-based material for example, which can be overmoulded on the plug 51 and integral or glued to the sheath 32. The protective shell 34 may be retained on plug 51 by material insertion into recesses (not shown) arranged on the outer surface of the plug body 51a. A plug head 51b extends outwardly from said body 51a outside the protective shell 34. The plug 51 has an open inner channel or tube 51c extending over the full length thereof, wherein a connecting rod 52 is fitted, said connecting rod comprising a crenelated part 52a housed in the plug's body 51a and a connecting head 52b extending through the plug's head 51b. Wire 31 is passed in a lumen or capillary in the connecting rod 52 and its knot 312, is received in an end recess 52c in the connecting head 52b. Wire 31 are thus fastened to the connecting rod 52, which will mechanically link the transmission 3 to the actuator 7 as will be described herein after, Advantageously, the connecting rod 52 can translate within the plug 51 so as to allow tensile strength applied on the connecting rod 52 by the actuator 7 to contract, respectively release, wire 31 in the flexible transmission 3 and thereby the contractile element 11. That displacement capability can however be limited by the toothed configuration of the crenelated part, which engages with inner hooking members radially extending internally from the plug's body 51a upon application of a pressure as shown by arrows F in FIG. 5 Activation of the hooking members allows to lock the connecting rod 52 in position to allow manual disconnection of the connector 5 from the actuator 7 without over-constricting the contractile element around the urethra. This locking mechanism of the connecting rod 52 allows to transfer any pulling/pushing action on the connector 5 only to the plug 51 and not to the wire 31 in the flexible transmission, thereby permitting safe connection and disconnection of the actuator for the constricted organ.

The head 51b of the plug 51 is cylindrical and is a sliding fit within a tube socket 7c extending from the housing of the control system. Upon insertion of the plug head 51b into the socket 7c the connecting head 52b attaches to a distal extremity 7d of the screw-type actuator 7b by any convenient attachment. In the illustrated embodiment, a first coil spring 71 held within a corresponding first annular groove 71g in the distal extremity 7d of the screw-type actuator 7b cooperates in a corresponding groove 52d arranged on the outer surface of the connecting head 52b. As an alternative, an O-ring may be used instead of a coil spring. Upon insertion of the connecting head 52b in the distal extremity 7d of the screw-type actuator 7b, the coil spring 71 clips into the annular groove 52d so as to retain the connecting head 52b and plug 51 upon the distal extremity of the screw-type actuator 7 and to transmit force and movement thereto. In this sense, the toroidal spring provides a kinematic link between the connecting rod 52 and the distal extremity of the actuator 7. As a variation, the position of the two annular grooves 71g, 52d can be inverted if desired, the coil spring 71 thereby being supported in the connecting head 52b and clipping into the groove in the distal extremity 7d of the actuator 7.

In order to support the outer sheath 32 of the flexible transmission 3, a distal end of the protective shell 31 of the connector forms a hollow end cap fixed upon the outside of sheath 32 by means of a further toroidal spring 54 provided in between the wire 31 and the sheath 32 on the one end and a seat 55 arranged between a distal end of the crenelated part 52a of the connecting rod 52 and the distal end of the cavity 51c. The wire 31 pass through an axial passage in the seat 55. The seat 55 is preferably made of a polymer with low friction and a smaller lumen diameter than the toroidal spring it is guiding to prevent the wire 31 for wearing-off. This is particularly advantageous as the toroidal spring 54 may present sharp edges. The seat 55 is also designed and press-fit or screwed-in to 51a so as to resist the push force generated when connecting the plug's head 52d into the screw-type actuator 7b.

In order to minimise ingress of fluid between connector 5 and the socket tube 7c and to securely maintain the plug 51 into the socket 7c one or more (in the present one of each) coil spring(s) 72 and sealing ring(s) 76 are provided in corresponding grooves in an inner wall of the socket tube 7c, in contact with the outer part of the plug head 51b.

FIG. 6 illustrates an embodiment of a wire coil 18 formed of double wire coils 18a, 18b around wire 31. It can clearly be seen on that figure that inner wire coil 18a is wound in a first direction around wire 31, and outer wire coil 18b surrounding the inner wire coil 18a, is wound in a second direction opposite to the first direction. Such a double-coil arrangement helps to prevent kinking of the transmission portion of the tensioning device 2 and helps reduce the risk of rupture. It also prevents coil pinching each other when bending the transmission. Outer wire coil 18b and optionally also inner wire coil 18a may be attached at a first end to anchoring plate 45 and at a second end form or attach to toroidal spring 54 in the seat 55 of the connector 5.

Furthermore, as a simpler alternative, wire coil 18 may be formed as a single coil or further alternatively, a multi-layer coil comprising more than two coils can be used.

An alternate arrangement of tensioning device 2, not illustrated, incorporates a pair of wires 31 arranged so as to operate in opposite directions, such that pulling on a first wire tightens the contractile element 1, whereas pulling on the second wire loosens the contractile element 1.

In contrast to the prior art cuffs referenced above, the contractile element 1 is not merely tightened by reducing its circumference in the manner of a slipknot or by twisting wires together. When a tensile force is applied by tensioning device 2, second anchor point B is pulled towards first anchor point A, tightening the wire 31 down on the flexible strip 4. This causes the contractile element 1 to flex, the transversal reinforcement elements 42 resisting this flexion and causing the contractile element 1 to curve gently in its cross-section broadly into a U-shape or U-like-shape rather than the aggressive V-shape that would be taken by the cross-section of the contractile element 1 in the case in which the transversal reinforcement elements were not present. In consequence, a gentle pressure is applied to the hollow body organ over as large an area as possible, reducing tissue damage.

As a result, the contractile element 1 cannot pinch underlying tissue, and applies a pressure of at most 8 N/cm2, preferably at most 5 N/cm2, further preferably at most 2 N/cm2. Furthermore, due to the way in which the flexible strip 4 deforms to apply pressure, this pressure is particularly uniform around the circumference of the flexible strip, and varies by at most 15%, preferably by at most 10%, preferably by at most 5% along the flexible strip 4 where it is in contact with the hollow body organ when the contractile element 1 is activated.

FIGS. 1A-1B illustrate a contractile element 1 assembled with a tensioning device 2 with its flexible transmission 3 attached to connector 5, ready for implantation. In use the artificial contractile device of the invention can be implanted in a patient by laparoscopy surgery, the contractile element 1, its tensioning device 2 and connector 5 being manipulated with a trocar. The contractile element 1 is formed in a loop about a hollow body organ such as a urethra by inserting connector 5 in the pass-through opening 63 of closure 6 and pulling on said connector until the proximal part 32a of the outer sheath at the flexible strip enters said closure 6. This proximal part 32a corresponds advantageously to a setting section for adjusting the diameter of the contractile element about the urethra, and also to that of so-called dead-zone of the contractile element 1, i.e. a zone that hardly contracts upon application of tensile force tension on wire 31 by an actuator. To set the diameter of contractile element 1 one simply needs to press tab 61 onto the proximal part 32a at the desired position so as to plug reinforcement elements 42 into locking slots 62 of closure tab 61. This can be done easily with a trocar.

To help manipulation and hygiene during this operation the connector may advantageously be fitted with a screwable cap 56 having a tapered, corrugated, end for easing insertion in closure 6 and pulling with a trocar. When the diameter of contractile element 1 is set about the hollow body organ the surgeon pulls the connector 5 and transmission to a subcutaneous connection site where an actuator 7 is implanted and then said screwable cap 56 is manually unscrewed and connector 5 connected by push fitting it in actuator 7 as previously described.

A suitable actuator 7 (see FIG. 5) with which the contractile element 1 is used may be an actuator corresponding to those disclosed in any of the documents WO13091730, WO13093074 or WO12000681, or any other convenient actuator.

The invention claimed is:

1. An artificial contractile structure comprising:

at least one contractile element comprising:

a flexible strip extending in a longitudinal directional, said flexible strip having a plurality of transversal reinforcement elements extending from a surface thereof opposite a smooth surface arranged for contacting a hollow body organ, and a closure for forming the at least one contractile element into a closed loop around the hollow body organ, the closure being situated at a first extremity of the flexible strip, the at least one contractile element being adapted to contract the hollow body organ, in such a way that said at least one contractile element is adapted to be in a resting position or in an activated position, the activated position being defined with said at least one contractile element constricting the hollow body organ and the resting position being defined with said at least one contractile element not constricting the hollow body organ, characterized in that the contractile structure further comprises:

a flexible transmission comprising a tensioning element being anchored at a first end to a first anchoring point on the flexible strip, wherein said tensioning element passes through at least some of the transversal reinforcement elements, said flexible transmission being adapted to tighten the at least one contractile element formed in a closed loop around said hollow body organ upon application of a traction force at an end of the tensioning element by an actuator, and a connector adapted to connect the flexible transmission to said actuator, a second end of said tensioning element being anchored in said connector.

2. The artificial contractile structure according to claim 1, wherein the tensioning element is covered with a flexible sheath.

3. The artificial contractile structure according to claim 1, wherein the flexible strip comprises a plurality of openings, each opening being situated between two adjacent transversal reinforcement elements.

4. The artificial contractile structure according to the claim 3, wherein the tensioning element is a filament, a wire, a cable or a flat strip.

5. The artificial contractile structure according to claim 2, wherein the sheath comprises at least one coiled wire.

6. The artificial contractile structure according to claim 5, wherein the at least one coiled wire of the sheath comprises an inner coiled wire coiled in a first direction, and an outer coiled wire surrounding the inner coiled wire and coiled in a second direction opposite to said first direction.

7. The artificial contractile structure according to the claim 6, wherein the closure is arranged so as to form the at least one contractile element into a closed loop having one of a plurality of predetermined circumferences.

8. The artificial contractile structure according to claim 7, wherein the closure comprises a tab at an end of the flexible strip and connected thereto by two connecting side walls integrally formed with the tab and flexible strip in order to define a pass-through hole for passing said flexible transmission and connector to form the at least one contractile element in the closed loop around said hollow body organ.

9. The artificial contractile structure according to claim 8, wherein the connector is configured for allowing a push-fit connection to the actuator.

10. The artificial contractile structure according to claim 9, wherein said connector comprises a helicoidal spring or an o-ring linking a first annular groove provided in one of said actuator and said connector and providing a kinematic link with a further annular groove provided in an other of said actuator and said connector.

11. The artificial contractile structure according to claim 9, wherein the connector comprises a connecting rod longitudinally movable within a coaxial plug, said connecting rod being attached to said tensioning element.

12. The artificial contractile structure according to claim 11, wherein the connecting rod comprises a crenelated part cooperating with releasable hooking members of said plug to allow movement of the connecting rod in said plug.

13. A medical device, comprising an artificial contractile device and an actuator, the artificial contractile device comprising at least one contractile element comprising a flexible strip extending in a longitudinal direction and a closure for forming the at least one contractile element into a closed loop around a hollow body organ, the closure being situated at a first extremity of the flexible strip, the at least one contractile element being adapted to contract a hollow body organ, in such a way that said at least one contractile element is adapted to be in a resting position or in an activated position, the activated position being defined with said at least one contractile element constricting the hollow body organ and the resting position being defined with said at least one contractile element not constricting the hollow body organ, characterized in that the artificial contractile device further comprises:

a flexible transmission comprising a tensioning element being anchored at a first end to a first anchoring point on the flexible strip, said flexible transmission being adapted to tighten the at least one contractile element formed in the closed loop around said hollow body organ upon application of a traction force at an end of the tensioning element by the actuator, and a connector adapted to connect the flexible transmission to said actuator, a second end of said tensioning element being anchored in said connector, the actuator comprising a connection socket configured for a push-fit connection with said connector, wherein said connector comprises a helicoidal spring or an o-ring linking a first annular groove provided in one of said actuator and said connector and providing a kinematic link with a further annular groove provided in an other of said actuator and said connector, said actuator comprising an actuating mechanism arranged to apply a tensile force to said tensioning element of the flexible transmission when said connector is connected into said socket.

14. The device according to claim 13, wherein the flexible strip comprises a plurality of transversal reinforcement elements extending from a surface thereof opposite a smooth surface arranged for contacting said hollow body organ.

15. The device according to claim 14, wherein the tensioning element passes through at least some of the transversal reinforcement elements.

16. The device according to claim 15, wherein the tensioning element is covered with a flexible sheath.

17. The device according to the claim 13, wherein the closure is arranged so as to form the at least one contractile element into a closed loop having one of a plurality of predetermined circumferences.

18. The device to claim 13, wherein the connector comprises a connecting rod longitudinally movable within a coaxial plug, said connecting rod being attached to said tensioning element.

* * * * *